United States Patent
Colle et al.

(10) Patent No.: US 8,163,825 B2
(45) Date of Patent: Apr. 24, 2012

(54) TRIGLYCERIDE PLASTICIZERS HAVING LOW AVERAGE LEVELS OF BRANCHING AND PROCESS OF MAKING THE SAME

(75) Inventors: Karla S. Colle, Houston, TX (US); Allen David Godwin, Seabrook, TX (US); Jon Edmond Stanat, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 382 days.

(21) Appl. No.: 12/542,407

(22) Filed: Aug. 17, 2009

(65) Prior Publication Data

US 2010/0056681 A1 Mar. 4, 2010

Related U.S. Application Data

(60) Provisional application No. 61/093,891, filed on Sep. 3, 2008.

(51) Int. Cl.
*C08K 5/103* (2006.01)
*C08K 5/101* (2006.01)

(52) U.S. Cl. ........ 524/312; 524/287; 524/306; 524/311; 524/313; 524/326

(58) Field of Classification Search .......... 524/287, 524/306, 311, 312, 313, 315, 326
See application file for complete search history.

(56) References Cited

U.S. PATENT DOCUMENTS

| | | | | |
|---|---|---|---|---|
| 2,327,128 A * | 8/1943 | Renfrew et al. | | 524/143 |
| 4,014,845 A * | 3/1977 | Grier et al. | | 524/104 |
| 4,392,581 A * | 7/1983 | Itsubo et al. | | 215/348 |
| 5,248,531 A * | 9/1993 | Nagai et al. | | 428/34.1 |
| 6,284,917 B1 | 9/2001 | Brunner et al. | | |
| 6,652,774 B2 | 11/2003 | Zhou et al. | | |
| 6,734,241 B1 | 5/2004 | Nielsen et al. | | |
| 6,740,254 B2 | 5/2004 | Zhou et al. | | |
| 6,777,514 B2 | 8/2004 | Patil et al. | | |
| 6,811,722 B2 | 11/2004 | Paul et al. | | |
| 7,297,738 B2 * | 11/2007 | Gosse et al. | | 524/285 |
| 7,413,813 B2 | 8/2008 | Gosse et al. | | |
| 2006/0247461 A1 | 11/2006 | Schlosberg et al. | | |
| 2007/0027244 A1 | 2/2007 | Schar et al. | | |
| 2007/0112220 A1 | 5/2007 | Caers et al. | | |

(Continued)

FOREIGN PATENT DOCUMENTS

WO  WO 03029339 A1 *  4/2003

OTHER PUBLICATIONS

Godwin, A.D. et al., "*Plasticizers*", Applied Polymer Science 21$^{st}$ Century, edited by C. D. Craver and C. E. Carraher, Elsevier (2000) pp. 157-175.

(Continued)

*Primary Examiner* — Satya Sastri

(74) *Attorney, Agent, or Firm* — Andrew B. Griffis; Leandro Arechederra, III

(57) ABSTRACT

Triglyceride PVC plasticizers can be produced by recovery of $C_5$ to $C_{10}$ aldehydes having low average levels of branching from a hydroformylation product, oxidizing the aldehydes with oxygen and/or air to form an acid, recovery of the resulting acid, and esterification with glycerol. Plasticizer compositions including such products or linear triglycerides combined with a secondary plasticizer and articles made therefrom are disclosed.

4 Claims, 1 Drawing Sheet

U.S. PATENT DOCUMENTS

2008/0242895 A1   10/2008   Godwin et al.

OTHER PUBLICATIONS

Shobha, H.K. et al., "*Structural Expressions of Long-Chain Esters on Their Plasticizing Behavior in Polyvinyl Chloride*", Macromolecules (1992) vol. 25, No. 25, pp. 6765-6769.

Riser, G.R. et al., "*A Method for Determining Compatibility Parameters of Plasticizers for Use in PVC Through Use of Torsional Modulus*", Polymer Engineering and Science (1967), pp. 110-114.

Alpha Olefins Applications Handbook (1989) CRC Press, pp. 311-327.

U.S. Appl. No. 61/040,480, filed Mar. 28, 2008, Godwin.

* cited by examiner

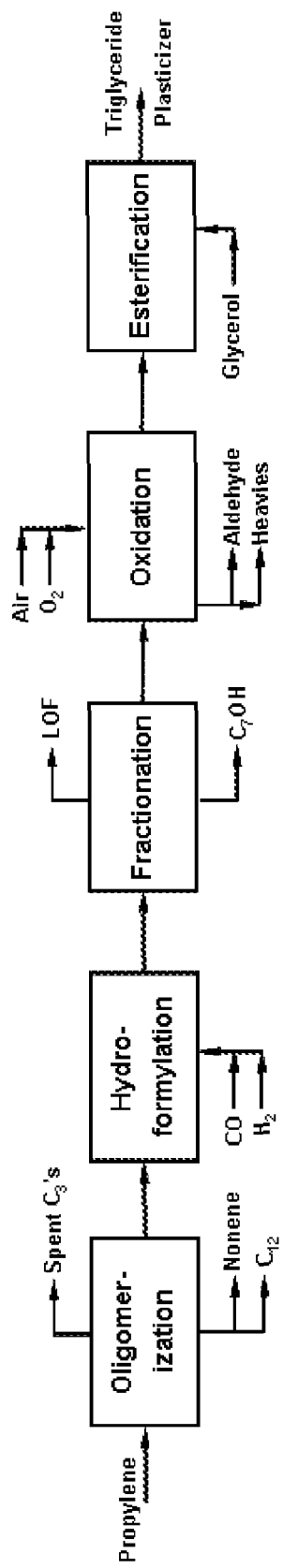

TRIGLYCERIDE PLASTICIZERS HAVING LOW AVERAGE LEVELS OF BRANCHING AND PROCESS OF MAKING THE SAME

PRIORITY CLAIM

This application claims priority to and the benefit of U.S. Ser. No. 61/093,891, filed Sep. 3, 2008.

FIELD OF THE INVENTION

The invention relates to triglyceride esters based on alkyl groups and processes for making them. More specifically, the invention relates to triglyceride esters having alkyl groups with low levels of branching.

BACKGROUND OF THE INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, poly(vinylidene chloride), nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there has been an effort to decrease the use of phthalate esters as plasticizers in PVC, particularly in end uses where the product contacts food, such as bottle cap liners, sealants, potable water tubing and food films, or for medical applications such as examination gloves, blood bags, and IV delivery systems, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Patent Publication No. 2006-0247461, and U.S. Pat. No. 7,297,738.

Other suggested substitutes include esters based on benzoic acid, see, for instance, U.S. Pat. No. 6,740,254, and also co-pending, commonly-assigned, U.S. Provisional Application No. 61/040,480, filed Mar. 28, 2008 and polyketones, such as described in U.S. Pat. No. 6,777,514; and also co-pending, commonly-assigned, U.S. application Ser. No. 12/058,397, filed Mar. 28, 2008. Epoxidized soybean oil, which has much longer alkyl groups ($C_{16}$ to $C_{18}$) has been tried as a plasticizer, but is generally used as a PVC stabilizer. At high concentrations, epoxidized soybean oil will eventually migrate to the surface of the plasticized PVC product and yield an unusable product.

Typically, the best that has been achieved with substitution of the phthalate ester with an alternative material is a flexible PVC article having either reduced performance or poorer processability. Thus, heretofore efforts to make phthalate-free plasticizer systems for PVC have not proven to be entirely satisfactory, and this is still an area of intense research.

Plasticizers based on triglycerides have been tried in the past, but they have mostly been based on natural triglycerides from various vegetable oils. The alkyl groups on these natural triglycerides are linear, and can cause compatibility problems when the alkyl chain is too long.

"Structural Expressions of Long-Chain Esters on Their Plasticizing Behavior in Polyvinyl Chloride", H. K. Shobha and K. Kishore, Macromolecules 1992, 25, 6765-6769, reported the influence of branching and molecular weight in long-chain esters in PVC. Triglycerides (TGE's) having alkyl groups were studied.

"A Method for Determining Compatibility Parameters of Plasticizers for Use in PVC Through Use of Torsional Modulus", G. R. Riser and W. E. Palm, Polymer Engineering and Science, April 1967, 110-114, also investigate the use of triglycerides and their plasticizing behavior with PVC, including tri-iso-valerin (3-methyl butanoate) triglyceride. This study reports that "these materials have volatilities that are much too high for good long-time permanence".

Nagai et al. in U.S. Pat. No. 5,248,531, teaches the use of articles comprising vinyl chloride-type resins (among others) using triglyceride compounds as a hemolysis depressant, and also comprising 10 to 45 wt. % of plasticizers selected from trialkyl trimellitates, di-normal alkyl phthalates, and tetraalkyl pyromellitates. The alkyl chains of the acid moiety $R^1$-$R^3$ in the structure below, formula (I), are independently an aliphatic hydrocarbon group of 1 to 20 carbon atoms and in embodiments at least one of the alkyl chains is branched. One specific triglyceride disclosed is glyceryl tri-2-ethylhexanoate.

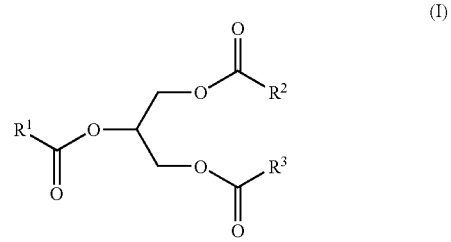

(I)

Zhou et al. discloses, in U.S. Pat. Nos. 6,652,774; 6,740,254; and 6,811,722; phthalate-free plasticizers requiring a mixture of different triesters of glycerin, preferably wherein the phthalate-free plasticizer is formed by a process of esterifying glycerin with a mixture comprising a mixture of alkyl acids and aryl acids.

Nielsen et al., in U.S. Pat. No. 6,734,241, teach a composition comprising a thermoplastic polymer as in formula (I) above, wherein at least one of the R groups is an alkyl group having from 1-5 carbon atoms and at least one of the R groups is a saturated branched alkyl group having from 9 to 19 carbon atoms and a hydrophilic group.

Among the problems presented by the aforementioned triglycerides is they cannot be made conveniently and thus generally are quite expensive and/or are specialty chemicals not suitable as replacements for phthalates from an economic standpoint and/or are not as compatible with the range of polymer systems that phthalates are compatible with, and thus are not viable replacements for phthalates from a physical property standpoint.

For instance, some synthesis methods involve at least two separate steps, such as where the glycerol is first partially esterified with the $C_{10}$ to $C_{20}$ branched chain acyl group and then reacted with acetic acid or acetic anhydride. Yet in another synthesis, a natural triglyceride ester such as that extracted from castor oil, may be partially saponified to obtain a monoester of glycerol, and then esterified with a shorter chain acid such as acetic acid.

Other syntheses involving mixed acid feeds will require addition of a hydrocarbon solvent for azeotropic distillation of the water to drive the esterification reaction to completion (as measured by the hydroxyl number of the ester, which is a measure of the amount of unreacted OH groups), due to the spread in boiling points between the mixed acids. In addition, the use of mixed acid feedstock such as cited in Zhou et al. and in Nielsen et al. can reduce the capability of recycling unreacted acids.

Triglycerides based on acids derived from natural products will be limited to naturally occurring alkyl groups with even carbon numbers, which offer very little flexibility in designing an appropriate plasticizer system for a given polymer system.

Thus what is needed is a method of making triglyceride esters based on alkyl groups that can be economically produced on a commercial scale, preferably for use as a plasticizer with suitable melting or pour point, increased compatibility, good performance and low temperature properties.

The present inventors have surprisingly discovered that triglyceride esters with alkyl chains having low average levels of branching may be produced by esterification of glycerol with acids derived from the hydroformylation and subsequent oxidation of $C_5$ to $C_9$ olefins. Esterification of glycerol using an acid mixture with a narrow carbon number range eliminates many of the aforementioned problems, and enables high yield of the glycerol triesters to be obtained, having low residual hydroxyl numbers.

As discussed above, there is also a need to improve the compatibility of existing plasticizers or provide alternative plasticizers having acceptable performance. To that end, the inventors have discovered that alkyl triglycerides may be used in combination with other alternative plasticizers to meet such a need.

SUMMARY OF THE INVENTION

In one aspect, embodiments of the invention are directed to a process comprising recovery of a $C_5$ to $C_{10}$ aldehyde composition from a hydroformylation process, preferably where the aldehydes have low average levels of branching; oxidation of the aldehyde composition to acids with oxygen and/or air; recovery of the resulting acid composition, and esterification with glycerol or other polyols. A similar result may be achieved by recovery of such $C_5$ to $C_{10}$ aldehydes from a hydroformylation process, hydrogenation to alcohols, then oxidation of the alcohols to acids, and subsequent esterification with glycerol or other polyols.

In preferred embodiments, the process further comprises providing a feed for the hydroformylation process from dimerization of diverse feedstock, preferably dimerization of a $C_3$ or $C_4$ feedstock, or mixture thereof. In some such embodiments, the level of branching is controlled by providing an optional source of one or more linear alkenes to the hydroformylation reaction.

In another embodiment, a $C_5$ to $C_{10}$ acid composition is provided at molar ratios of the acids to provide average carbon number between $C_7$ and $C_8$ for the mixture. In one such embodiment, a mixture of n-pentanoic acid and 2-propylheptanoic acid provides a triglyceride having alkyl groups with an average carbon number of about 7.5 with an averaged branching per acid molecule of 0.5.

In still another embodiment, the $C_5$ to $C_{10}$ acid composition is prepared and blended with a second acid composition to adjust the overall branching level. In some such embodiments, an acid composition having about 1.2 to about 1.6 or about 1.8 to 2.1 branches per acid molecule is blended with a linear carboxylic acid. The composition is then esterified with glycerol or other polyols. These plasticizing esters can be prepared by esterification of glycerol with a blend of 2-propyl heptanoic acid, or isononanoic acid or 2-ethyl hexanoic acid with n-pentanoic acid or n-hexanoic acid. In some embodiments the n-pentanoic acid is provided by an OXO process using Rhodium catalyst and butene-1 as a feed. N-hexanoic acid may be provided for example from saponification of natural triglcerides such as coconut oil.

In another embodiment, the process described herein uses $C_6$ linear alpha olefins. The olefins are subjected to a rhodium-based OXO process to provide a composition comprising about 75 wt. % to about 95% wt. % n-heptanoic acid and about 5 wt. % to about 25 wt. % 2-alkyl substituted $C_7$ acids. In some embodiments, the mixture is subjected to a distillation to adjust the composition to have from about 95 wt. % to about 99.5 wt. % linear $C_7$ acid. In some embodiments the linear $C_7$ acid comprises greater than 99% of the acid composition.

The invention is also directed to the product of the process of the invention, which comprises at least one compound represented by the formula (I)

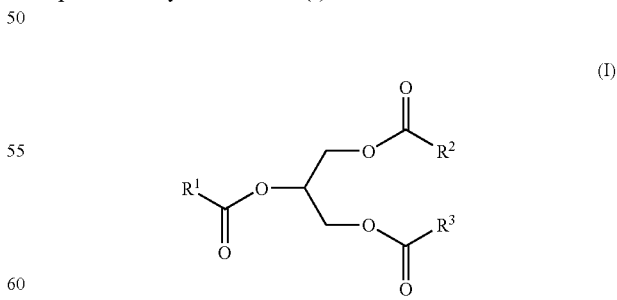

wherein $R^1$, $R^2$, and $R^3$ are independently selected from C4 to C10 alkyl groups having a low average level of branching of from about 0.05 to less than 0.8 branches per alkyl group in the molecule. In an embodiment, the average branching per alkyl group may range from about 0.1 to about 0.7. In another embodiment, the average branching of the C4 to C10 alkyl groups ranges from about 0.1 to about 0.6, preferably around about 0.2 to about 0.5, more preferably about 0.3 to 0.4 branches per alkyl group molecule. These averages are based on the sum total of alkyl groups on all $R^1$-$R^3$ side chains in all the polyols in the mixture.

In the specific case of $C_7$ triglycerides, the process of the invention provides, in preferred embodiments, an average branching of about 0.3 to 0.5, based on the branching in molecules having $C_6$ alkyl chains in each of $R^1$, $R^2$ and $R^3$. In the specific case of $C_9$ triglycerides, the process of the invention provides, in preferred embodiments, an average branching of about 0.2 to about 0.8, based on the branching in molecules having $C_8$ alkyl chains in each of $R^1$, $R^2$ and $R^3$.

In another aspect, embodiments of the invention are also directed to the product of the process of the invention, which comprises at least one compound represented by the formula (I) above, wherein $R^1$, $R^2$, and $R^3$ are independently selected from $C_4$ to $C_{10}$ alkyl groups.

In another aspect, embodiments of the invention are also directed to a composition comprising the product of the process of the invention and a resin.

In another aspect, embodiments of the invention are still further directed to an article comprising the composition according to the invention.

In another aspect, embodiments of the invention are directed to compositions that include a polymer, at least one alkyl triglyceride, and a secondary plasticizer. In such embodiments, linear alkyl triglycerides are suitable. In particular embodiments, however, alkyl triglycerides having low average levels of branching as described above may provide various benefits.

Additional and various independent features or advantages of specific embodiments of the invention will become apparent as reference is made to the following detailed description, preferred embodiments, examples, and appended claims.

BRIEF DESCRIPTION OF THE DRAWINGS

In the accompanying drawing, like reference numerals are used to denote like parts throughout the several views.

FIG. 1 is a schematic representation of a process according to a preferred embodiment of the invention.

DETAILED DESCRIPTION OF THE INVENTION

According to the invention, at least one linear triglyceride ester or triglyceride ester having low levels of branching on the alkyl chains is produced by esterification of one or more $C_5$ to $C_{10}$, preferably $C_6$ to $C_9$, acids with glycerol.

In preferred embodiments, the at least one $C_5$ to $C_{10}$, preferably $C_6$ to $C_9$, acids will be derived from the hydroformylation of light olefins ($C_5$ to $C_8$ olefins) and thus may be referred to herein as "oxo acids". The Oxo Process is per se well known. By way of recent examples, see, for instance, U.S. Pat. Nos. 7,345,212; 7,186,874; 7,148,388; 7,081,554; 7,081,553; 6,982,295; 6,969,736; 6,969,735; 6,013,851; 5,877,358; and PCT publications WO2007106215; WO2007040812; WO2006086067; WO2006055106; WO2003050070; WO2000015190. Typically, the hydroformylation of light olefins produces aldehydes which may be hydrogenated to the alcohol and subsequently oxidized to the desired acid(s), or directly oxidized to the desired acid(s). However, it will be recognized by one of skill in the art that acids may be derived from other processes.

Embodiments of the invention are also directed to the product of the process of the invention, which comprises at least one compound represented by formula (I)

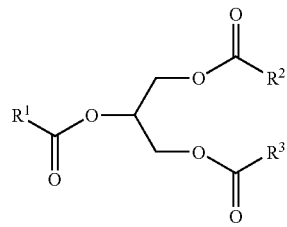

wherein $R^1$, $R^2$, and $R^3$ are independently selected from linear and branched $C_4$ to $C_{10}$ alkyl groups that provide the product with a low average level of branching of from about 0.05 to less than 0.8 branches per alkyl group in the molecule. In an embodiment, the average branching may range from about 0.07 to about 0.7. In another embodiment, the average branching of the $C_5$ to $C_{10}$ alkyl groups ranges from about 0.1 to about 0.6, preferably around about 0.2 to about 0.5, more preferably about 0.3 to 0.4 branches per alkyl group in the molecule.

The acids and esters described herein are typically mixtures of isomers or molecules having a different number of carbon atoms. For an example, a $C_9$ acid with an average branching number of 1.0 would refer to acids such as methyl substituted octanoic acids. A product incorporating 50/50 mixture of n-nonanoic acid and 2-methyl octanoic acid would have an average branching number of 0.5 branches per acid molecule. A product formed in the presence of a 70/30 mixture of n-nonanoic acid and 2-methyl octanoic acid would have an average branching number of 0.3 branches per acid molecule. It is believed that the low levels of branching provide benefits over triglycerides wherein the chains are all the same and linear.

In the specific case of $C_7$ triglycerides, the process of the invention provides, in preferred embodiments, an average branching of about 0.3 to 0.5 per alkyl chain, based on the branching in molecules having $C_6$ alkyl chains in each of $R^1$, $R^2$ and $R^3$. In the specific case of $C_9$ triglycerides, the process of the invention provides, in preferred embodiments, an average branching of about 0.2 to about 0.8, based on the branching in molecules having $C_8$ alkyl chains in each of $R^1$, $R^2$ and $R^3$.

The average branching numbers of the acids and esters described herein can be determined through techniques such as GC/MS where the structure of each isomer and its relative concentration in the mixture is determined. Alternatively, average branching numbers may be determined based on the sum total of alkyl groups on all $R^1$-$R^3$ side chains in all the polyols in the mixture using $^1H$ and $^{13}C$ NMR measurements of the esters or acids, through comparison of the methylene, methine, and quaternary carbons to the methyl carbons. For example, if the NMR measurements were to give peak ratios of two methyl carbon atoms to 1 carbonyl carbon atom to 1 methine carbon, to 3 methylene carbon atoms, the R side chain would be described as methyl pentyl group with 1 branching per alkyl group while the acid would be described as isoheptanoic acid.

NMR analyses of the branching found in the oxo acids shows that the branches are typically methyl branches. For example, with the branched $C_7$ oxo acid prepared in hydroformylation of isohexenes, typical isomers include n-heptanoic acid, 3-methyl hexanoic acid, 4-methyl hexanoic acid, 2-methyl hexanoic acid, as well as some 3,4-dimethyl pentanoic acid, and 2,4 dimethyl pentanoic acid. Similar products are found with mixtures of isomers in the $C_8$ oxo acids produced from heptenes. $C_9$ oxo acids when prepared from the OXO reaction using octenes produced from the dimerization of butenes, gives an isomeric mixture of methyl octanoic acids and dimethyl heptanoic acids with an average acid of 1.3 to 1.7 methyl groups per molecule. $C_9$ OXO acids prepared from the OXO reaction using linear octenes produced from the oligomerization of ethylene gives a mixture of n-nonanoic acid and 2-alkyl substituted acids such as 2-methyl octanoic acid, 2-ethyl heptanoic acid, 2-propyl hexanoic acid, and 2-butyl pentanoic acid with an average branching of 0.15 to 0.4 branches per acid molecule.

In a preceding step, aldehydes can be produced by hydroformylation of $C_4$ to $C_9$ higher olefins that in turn have been produced by propylene and/or butene oligomerization and/or ethylene oligomerization by any suitable method such as zeolite catalyzed oligomerization, the Dimersol process, the Octol process, or any other process that produces low levels of branching. Low levels of branching may also be obtained by supplying butene-1, pentene-1, hexene-1, heptene-1, octene-1, and nonene-1 directly to hydroformylation.

The resulting $C_5$ to $C_{10}$, preferably $C_6$ to $C_9$, aldehydes can then be recovered from the crude hydroformylation product stream by fractionation to remove unreacted olefins and the corresponding alcohols and other byproducts.

These $C_5$ to $C_{10}$, preferably $C_6$ to $C_9$, aldehydes can then in turn be oxidized to their respective $C_5$ to $C_{10}$, preferably $C_6$ to $C_9$, acids using air or enriched air as an oxygen source. In the alternative, the $C_5$ to $C_{10}$, preferably $C_6$ to $C_9$, aldehydes can be hydrogenated to the corresponding alcohol and then fully oxidized to the acid by oxidation or the alcohols can be converted to the aldehyde by catalytic dehydrogenation and then oxidized to the corresponding acid.

Following the oxidation reaction, the $C_5$ to $C_{10}$, preferably $C_6$ to $C_9$, acids can then be purified by fractionation to remove unreacted aldehydes and heavies formed during oxidation.

The $C_5$ to $C_{10}$, preferably $C_6$ to $C_9$, acids can then be esterified with glycerol or other alcohols including ethylene glycol, and other polyols.

Single carbon number acids can be used in the esterification, or acids of differing carbon numbers can be use to optimize product cost and performance requirements.

Glycerol is currently an attractive polyol for use to make plasticizers because it is abundantly available. It is, for instance, a co-product of biodiesel production and of natural alcohol production from coconut or palm kernel oil. Other polyols, however, may be utilized to produce plasticizers, such as ethylene glycol, propylene glycol, trimethylol propane, pentaerythritol, dipentaerythritol, and neopentyl glycol. Mixtures of polyols may be used, such as, but not limited too, a mixture of glycerol with propylene glycol or glycerol with trimethylol propane or glycerol with neopentyl glycol or pentaerythritol with dipentaerythritol.

It is preferred that the polyols be fully esterified so that there are a low to negligible amount of free hydroxyl groups. Thus, for example, it is preferred that glycerol is esterified to the triester.

The chemistry and a simplified process to produce triglycerides via the route described above are shown in equations (1)-(3), below. For simplicity, the hexene feed example is shown in eqn (1), but the feed can be pentenes, hexenes, heptenes, octenes, nonenes, or decenes as the starting olefins. As discussed above, the resulting $C_5$, $C_6$, $C_7$, $C_8$, $C_9$ and $C_{10}$ acids may be used individually or together in mixtures to make mixed carbon number esters to be used as plasticizers. This mixing of carbon numbers and levels of branching may be manipulated to achieve the desired compatibility with PVC for the respective polyol used for the polar end of the plasticizer, and to meet other plasticizer performance properties. While the exemplary gylceroltriheptanoate plasticizer shown in eqn. 3 has 1.0 branch per alkyl group in the molecule, it is apparent that this molecule represents a just one component in the plasticizer product mixture. Other components having one or more linear chains are also present at level that result in overall branching levels of 0.05 to 0.8 branches per alkyl chain in the molecule.

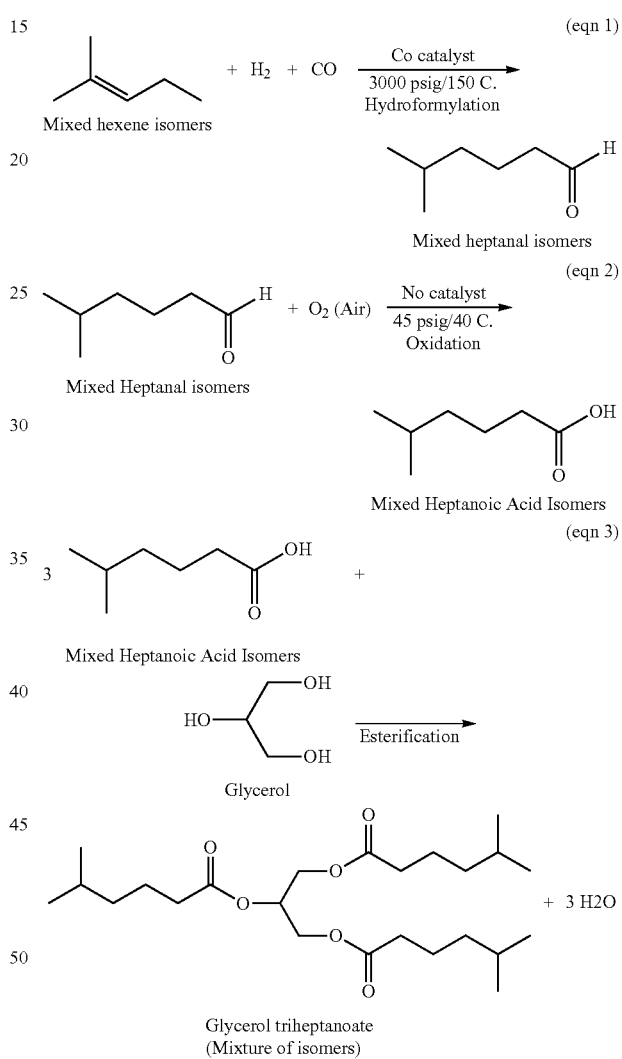

The applicability of the triglyceride structures as potential PVC plasticizers can be screened by estimating their relative solubility in PVC using Small's group contribution method to calculate solubility parameters for each structure (see The Technology of Plasticizers by J. Sears and J. Darbey, John Wiley & Sons, New York, 1982, pp 95-99, discussing using the Small formula for estimating plasticizer compatibility with PVC; this paper sites as a reference, the original work by Small: Small, P. A., "Some Factors Affecting the Solubility of Polymers", J. Appl. Chem., 3, pp 76-80 (1953); see also using Small's group contribution values from the Polymer Handbook, 3rd Ed., J. Brandrup & E. H. Immergut, Eds. John Wiley, New York, (1989)). These calculations are shown below in Table 1 for the C6 triglyceride:

TABLE 1

$C_6$ Triglyceride

|  | Solubility | Number | Solubility Contrib | MW | MW Contrib |
|---|---|---|---|---|---|
| $CH_3$ | 214 | 6 | 1284 | 15 | 90 |
| —$CH_2$— | 133 | 8 | 1064 | 14 | 112 |
| —CH= | 28 | 4 | 112 | 13 | 52 |
| COO esters | 310 | 3 | 930 | 44 | 132 |
|  |  |  | 3390 |  | 386 |
| Solubility Parameter = |  |  | 8.43 | Density = | 0.96 |
| Delta to PVC = |  |  | −1.23 |  |  |

Likewise, they may also be calculated for the $C_7$ triglyceride, shown in Table 2:

TABLE 2

$C_7$ Triglyceride

|  | Solubility | Number | Solubility Contrib | MW | MW Contrib |
|---|---|---|---|---|---|
| $CH_3$ | 214 | 6 | 1284 | 15 | 90 |
| —$CH_2$— | 133 | 11 | 1463 | 14 | 154 |
| —CH= | 28 | 4 | 112 | 13 | 52 |
| COO esters | 310 | 3 | 930 | 44 | 132 |
|  |  |  | 3789 |  | 428 |
| Solubility Parameter = |  |  | 8.50 | Density = | 0.96 |
| Delta to PVC = |  |  | −1.16 |  |  |

Table 3 shows the values calculated by the same method for the $C_8$ triglyceride:

TABLE 3

$C_8$ Triglyceride

|  | Solubility | Number | Solubility Contrib | MW | MW Contrib |
|---|---|---|---|---|---|
| $CH_3$ | 214 | 6 | 1284 | 15 | 90 |
| —$CH_2$— | 133 | 14 | 1862 | 14 | 196 |
| —CH= | 28 | 4 | 112 | 13 | 52 |
| COO esters | 310 | 3 | 930 | 44 | 132 |
|  |  |  | 4188 |  | 470 |
| Solubility Parameter = |  |  | 8.55 | Density = | 0.96 |
| Delta to PVC = |  |  | −1.11 |  |  |

Table 4 shows the values calculated by the same method for the $C_9$ triglyceride:

TABLE 4

$C_9$ Triglyceride

|  | Solubility | Number | Solubility Contrib | MW | MW Contrib |
|---|---|---|---|---|---|
| CH3 | 214 | 6 | 1284 | 15 | 90 |
| —CH2— | 133 | 17 | 2261 | 14 | 238 |
| —CH= | 28 | 4 | 112 | 13 | 52 |
| COO esters | 310 | 3 | 930 | 44 | 132 |
|  |  |  | 4587 |  | 512 |
| Solubility Parameter = |  |  | 8.6 | Density = | 0.96 |
| Delta to PVC = |  |  | −1.06 |  |  |

The solubility parameter of PVC is calculated by the same Small's Group Contribution Method to be 9.66. The differences in solubility parameters between the triglyceride structures in Formula I and PVC are shown in Table 1. These differences from PVC range from 1.23 for the $C_6$ triglyceride to 1.06 units for the $C_9$ triglyceride, which indicates reasonable expected solubility in PVC for these materials. As references, the solubility parameters for two well-known phthalate plasticizers, di-isononyl phthalate (DINP) and di-isodecyl phthalate (DIDP) are 8.88 (delta to PVC=0.78), and 8.56 (delta to PVC=1.10) respectively. The estimated solubility parameter for one non-phthalate plasticizer, di-isononyl cyclohexanoate, is 7.32 by Small's method. This is a difference of 2.34 solubility parameter units from PVC.

An illustration of an embodiment of the invention is illustrated in FIG. 1. Propylene is used as feedstock to an oligomerization reaction. The reaction may be continuous, batch, or semibatch. Unreacted $C_3$ olefins are distilled off and optionally recycled. Trimers and tetramers may be recovered as bottoms product with the desired dimer hexene taken as a sidestream and sent to the hydroformylation reaction. Branching levels may be adjusted by addition of an optional feed to the hydroformylation reaction, typically although not necessarily, of a linear olefin, such as 1-hexene or 1-octene. Carbon monoxide and hydrogen, conveniently supplied as Syngas, are also supplied to the reactor. The products are then separated by fractionation, with light olefins optionally recycled and the $C_7$ aldehydes and $C_7$ alcohols being separated. The amount of aldehyde and alcohols produced may be attenuated in the hydrofinishing section. In an embodiment, the $C_7$ aldehydes are then oxidized with the addition of air and/or oxygen, and unreacted aldehydes and heavies are separated out. The desired product $C_7$ acid is then esterified with polyol, in this embodiment glycerol and recovered as the triglyceride.

The plasticizers according to embodiments of the invention may also be used with vinyl chloride-type resins, polyesters, polyurethanes, ethylene-vinyl acetate copolymer, rubbers, acrylics, polymer blends such as of polyvinyl chloride with an ethylene-vinyl acetate copolymer or polyvinyl chloride with a polyurethane or ethylene-type polymer.

Now describing another aspect of the invention, linear alkyl triglycerides and alkyl triglycerides having low average levels of branching may be used in combination with a secondary plasticizer in the polymers described above. In these applications a broad definition of the term secondary plasticizer is implied, referring to another plasticizer or plasticizers used in combination with the inventive plasticizer. In this context, the plasticizers designated as secondary plasticizers often have utility as the primary plasticizer, when used at higher percentages in the plasticizer system, and in many cases, they can be used as the sole plasticizer in a flexible PVC product. Applicants have discovered that linear alkyl triglycerides combined with secondary plasticizers may result in compositions having improved properties when compared to compositions that where the secondary plasticizer or the linear alkyl triglyceride is substantially absent.

Additionally, alkyl triglycerides having low levels of branching may result in improved compositions when used in place of or along with linear alkyl triglycerides in the presence of a secondary plasticizer and a polymer.

One such secondary plasticizer comprises at least one ester selected from the group consisting of $C_4$, $C_5$, $C_6$, and $C_7$ secondary aliphatic alcohol esters of cyclohexanecarboxylic acid. Such secondary plasticizers are described in co-pending, commonly-assigned, U.S. Provisional Application No. 60/991,307, entitled "Compositions Based On $C_4$ to $C_7$ Secondary Aliphatic Alcohol Esters Of Cyclohexanecarboxylic Acids", filed Nov. 30, 2007 and is incorporated herein by reference in its entirety. Consistent with it's definition therein, the term cyclohexanecarboxylic acid esters as used herein is intended to include the cyclohexane group having at least one carboxylic acid functional group attached directly to the $C_6$ ring, thus including monocarboxylic acid and polycarboxylic acid groups, i.e., dicarboxylic acids, tricarboxylic acids, and so on. The preferred embodiment is the cyclohexanedicarboxylic acid ester of at least one $C_4$ to $C_7$ secondary aliphatic alcohols. All possible isomers of polycarboxylic acids are envisioned to be useful, however in preferred embodiments, the dicarboxylic acid isomer with the carboxylic acid groups in the 1,2 substitution position is the preferred isomer. Mixtures of isomers are also envisioned.

In preferred embodiments, the alkyl triglycerides described herein are combined with cyclohexanedicarboxylic acid esters of at least one $C_4$ to $C_7$ secondary aliphatic alcohols described above to provide a faster fusing plasticizer system, and even more particularly, they are useful as fast fusing plasticizers in mixtures with slower fusing plasticizers and/or with weaker solvating plasticizers, especially slower fusing plasticizers (or plasticizers with reduced solvency) such as di-2-propylheptyl phthalate or di-isononyl cyclohexanedicarboxylic acid esters or di-2-ethylhexyl terephthalate or di-2-propylheptyl cyclohexanedicarboxylic acid esters or other C10 to C13 dialkyl phthalate esters, to improve processability of PVC compositions. Fast fusing plasticizer or plasticizer systems are those plasticizers which solvate, dissolve, or fuse the PVC resin system faster or at lower temperatures relative to the industry standard plasticizer, di-2-ethylhexyl phthalate. Slower fusing plasticizers generally have poorer solvency for the PVC resin and require higher processing temperatures or longer heating times. In some such plasticizer compositions, the alkyl triglyceride composition comprises from about 1 wt % to about 99 wt % and the cyclohexanedicarboxylic acid esters comprise from about 99 wt % to about 1 wt % of the plasticizer composition, based on the combined weights of the alkyl triglyceride composition and cyclohexanedicarboxylic acid esters. In other embodiments, the lower limit of the alkyl triglyceride composition in the plasticizer compositions is at least about 10 wt %, at least about 20 wt %, at least about 30 wt %, at least about 40 wt %, at least about 50 wt %, at least about 60 wt %, at least about 65 wt %, at least about 70 wt %, at least about 75 wt %, at least about 80 wt %, at least about 85 wt %, at least about 90 wt %, or at least about 95 wt % of the plasticizer composition based on the amounts of the alkyl triglyceride composition and the cyclohexanedicarboxylic acid esters. The upper limit of the alkyl triglyceride composition in the plasticizer compositions can be less than about 10 wt %, less than about 20 wt %, less than about 30 wt %, less than about 40 wt %, less than about 50 wt %, less than about 60 wt %, less than about 65 wt %, less than about 70 wt %, less than about 75 wt %, less than about 80 wt %, less than about 85 wt %, less than about 90 wt %, or less than about 95 wt % of the plasticizer composition based on the amounts of the alkyl triglyceride composition and the cyclohexanedicarboxylic acid esters. In some embodiments the plasticizer composition comprises from about 10 wt % to about 90 wt %, about 20 wt % to about 80 wt %, 30 wt % to about 70 wt %, about 40 to about 60 wt %, or about 45 wt % to about 55 wt % of the alkyl triglyceride composition, based on the amounts of the alkyl triglyceride composition and cyclohexanedicarboxylic acid esters. Other specific compositions include compositions having combinations of the upper and lower limits enumerated above.

The combination of alkyl triglycerides described herein and cyclohexanedicarboxylic acid esters are also particularly useful in blends with other plasticizers, such as phthalates, benzoates, polyester polymeric plasticizers prepared, for instance, from the condensation of adipic acid with other polyols, alcohols, and acids, various acetylated citrate esters of C4 to C7 alcohols, other cyclohexanedicarboxylic acid esters, and terephthalates, which in embodiments improves the processability and/or the properties of PVC compounds based in part on those plasticizers. Such combinations are particularly useful in plastisol compositions. In embodiments, they offer advantages of yielding lower plastisol viscosities versus those plasticizers prepared from 1-substituted branched chain (primary) alcohols such as di-isoheptyl phthalate, di-isononylcyclohexanedioate, di-isononyl phthalate, di-2-propyl heptyl phthalate, or di-isodecyl phthalate, and may help reduce the fusion temperature. In some such plasticizer compositions, the alkyl triglyceride composition comprises from about 1 wt % to about 99 wt %, based on the combined weights of the alkyl triglyceride composition and other plasticizers in the plasticizer composition. In other embodiments, the lower limit of the alkyl triglyceride composition in the plasticizer compositions is at least about 10 wt %, at least about 20 wt %, at least about 30 wt %, at least about 40 wt %, at least about 50 wt %, at least about 60 wt %, at least about 65 wt %, at least about 70 wt %, at least about 75 wt %, at least about 80 wt %, at least about 85 wt %, at least about 90 wt %, or at least about 95 wt % of the plasticizer composition based on the combined weights of the alkyl triglyceride composition and other plasticizers in the plasticizer composition. The upper limit of the alkyl triglyceride composition in the plasticizer compositions can be less than about 10 wt %, less than about 20 wt %, less than about 30 wt %, less than about 40 wt %, less than about 50 wt %, less than about 60 wt %, less than about 65 wt %, less than about 70 wt %, less than about 75 wt %, less than about 80 wt %, less than about 85 wt %, less than about 90 wt %, or less than about 95 wt % of the plasticizer composition based on the combined weights of the alkyl triglyceride composition and other plasticizers in the plasticizer composition. In some embodiments the plasticizer composition comprises from about 10 wt % to about 90 wt %, about 20 wt % to about 80 wt %, 30 wt % to about 70 wt %, about 40 to about 60 wt %, or about 45 wt % to about 55 wt % of the alkyl triglyceride composition, based on the combined weights of the alkyl triglyceride composition and other plasticizers in the plasticizer composition. Other specific compositions include compositions having combinations of the upper and lower limits enumerated above.

Another such secondary plasticizer that may be combined with the alkyl triglycerides herein is described in co-pending, commonly-assigned, U.S. Provisional Application No. 60/991,314, entitled "$C_7$-$C_{12}$ Secondary Alcohol Esters Of Cyclohexanoic Acid", filed Nov. 30, 2007 and incorporated herein by reference in its entirety. In embodiments, the compositions comprise at least one $C_7$-$C_{12}$ secondary alcohol esters of cyclohexanecarboxylic acids, and at least one plasticizable polymer, such as PVC, polyurethanes, acrylics, and polyolefins. Particularly preferred are PVC compositions with at least one $C_7$ to $C_{12}$ secondary alcohol ester of a cyclohexanedicarboxylic acid. In preferred embodiments, compositions comprise at least one alkyl triglyceride and at least one cyclohexanecarboxylic acid ester, cyclohexanedicarboxylic acid ester or cyclohexanetricarboxylic acid ester prepared from at least one $C_7$ to $C_{12}$ secondary alcohols and PVC. In other preferred embodiments, at least one alkyl triglyceride is combined with dicarboxylic acid esters based on the 1,2- or 1,4-cyclohexandedicarboxylic acid esters of $C_7$ to $C_{12}$ secondary alcohols. In still other preferred embodiments at least one alkyl triglyceride is combined with at least one $C_7$ to $C_{12}$ secondary alcohol esters of cyclohexanecarboxylic acids prepared using linear secondary alcohols derived from linear internal olefins and linear alpha olefins. In still other preferred embodiments, at least one alkyl triglyceride is combined with at least one $C_7$ to $C_{12}$ secondary alcohol esters prepared from branched secondary alcohols derived from lightly branched olefins. In some such plasticizer compositions, the alkyl triglyceride composition comprises from about 1 wt % to about 99 wt %, based on the combined weights of the alkyl triglyceride composition and the at least one cyclohexanecarboxylic acid ester, cyclohexanedicarboxylic acid ester or cyclohexanetricarboxylic acid ester prepared from at least one $C_7$ to $C_{12}$ secondary alcohols in the composition. In other embodiments, the lower limit of the alkyl triglyceride composition in the compositions is at least about 10 wt %, at least about 20 wt %, at least about 30 wt %, at least about 40 wt %, at least about 50 wt %, at least about 60 wt %, at least about 65 wt %, at least about 70 wt %, at least about 75 wt %, at least about 80 wt %, at least about 85 wt %, at least about 90 wt %, or at least about 95 wt % of the plasticizer composition based on the combined weights of the alkyl triglyceride composition and the at least one cyclohexanecarboxylic acid ester, cyclohexanedicarboxylic acid ester or cyclohexanetricarboxylic acid ester prepared from at least one $C_7$ to $C_{12}$ secondary alcohols. The upper limit of the alkyl triglyceride composition in the plasticizer compositions can be less than about 10 wt %, less than about 20 wt %, less than about 30 wt %, less than about 40 wt %, less than about 50 wt %, less than about 60 wt %, less than about 65 wt %, less than about 70 wt %, less than about 75 wt %, less than about 80 wt %, less than about 85 wt %, less than about 90 wt %, or less than about 95 wt % of the composition based on the combined weights of the alkyl triglyceride composition and at least one cyclohexanecarboxylic acid ester, cyclohexanedicarboxylic acid ester or cyclohexanetricarboxylic acid ester prepared from at least one $C_7$ to $C_{12}$ secondary alcohols. In some embodiments the composition comprises from about 10 wt % to about 90 wt %, about 20 wt % to about 80 wt %, 30 wt % to about 70 wt %, about 40 to about 60 wt %, or about 45 wt % to about 55 wt % of the alkyl triglyceride composition, based on the combined weights of the alkyl triglyceride composition and at least one cyclohexanecarboxylic acid ester, cyclohexanedicarboxylic acid ester or cyclohexanetricarboxylic acid ester prepared from at least one $C_7$ to $C_{12}$ secondary alcohols. Other specific compositions include compositions having combinations of the upper and lower limits enumerated above.

Yet another such secondary plasticizer that may be combined with the alkyl triglycerides herein is described in co-pending, commonly-assigned, U.S. Provisional Application No. 61/015,962, entitled "Co-Plasticizer Systems", filed Dec. 21, 2007 and incorporated herein by reference in its entirety. Such co-plasticizer systems include cyclohexanedicarboxylic acid ester and/or cyclohexanepolycarboxylic acid esters and at least one fast fusing plasticizer. In preferred embodiments, compositions according to the invention comprise at least one slow fusing plasticizer selected from at least one cyclohexane dioate or cyclohexanoate trioate esters based on at least one alcohol selected from $C_8$ to $C_{11}$ aliphatic primary alcohols. Particularly preferred are the diisononyl and/or diisodecyl and/or di-2-propylheptyl esters. In other preferred embodiments, the slow fusing plasticizers are cyclohexanecarboxylic acid esters based on the 1,2- or 1,4 cyclohexanedicarboxylic acid esters. In yet still other preferred embodiments, the fast fusing plasticizer is selected from fast fusing esters based on di-butyl terephthalates, $C_8$ to $C_{10}$ mono benzoates, dibenzoates esters of ethylene glycol or dipropylene glycol, $C_4$ to $C_7$ cyclohexanoates, alkyl sulfonic acid esters of phenol, aliphatic dibutyrate esters, or citrate esters of $C_4$ to $C_6$ primary alcohols. In other embodiments, these plasticizing systems comprising a slow fusing plasticizer based on at least one cyclohexane dicarboxylic acid ester and at least one fast fusing plasticizer plastisol formulations to provide low viscosity formulations with improved viscosity stability and improved processability. Such combinations of plasticizers may be combined with the alkyl triglycerides described herein to provide a plasticizer composition wherein, the alkyl triglyceride composition comprises from about 1 wt % to about 99 wt %, based on the combined weights of the alkyl triglyceride composition and the combination of cyclohexanedicarboxylic acid ester and/or cyclohexanepolycarboxylic acid esters and at least one fast fusing plasticizer. In other embodiments, the lower limit of the alkyl triglyceride composition in the plasticizer compositions is at least about 10 wt %, at least about 20 wt %, at least about 30 wt %, at least about 40 wt %, at least about 50 wt %, at least about 60 wt %, at least about 65 wt %, at least about 70 wt %, at least about 75 wt %, at least about 80 wt %, at least about 85 wt %, at least about 90 wt %, or at least about 95 wt % of the plasticizer composition based on the combined weights of the alkyl triglyceride composition and the combination of cyclohexanedicarboxylic acid ester and/or cyclohexanepolycarboxylic acid esters and at least one fast fusing plasticizer. The upper limit of the alkyl triglyceride composition in the plasticizer compositions can be less than about 10 wt %, less than about 20 wt %, less than about 30 wt %, less than about 40 wt %, less than about 50 wt %, less than about 60 wt %, less than about 65 wt %, less than about 70 wt %, less than about 75 wt %, less than about 80 wt %, less than about 85 wt %, less than about 90 wt %, or less than about 95 wt % of the plasticizer composition based on the combined weights of the alkyl triglyceride composition and the combination of cyclohexanedicarboxylic acid ester and/or cyclohexanepolycarboxylic acid esters and at least one fast fusing plasticizer. In some embodiments the plasticizer composition comprises from about 10 wt % to about 90 wt %, about 20 wt % to about 80 wt %, 30 wt % to about 70 wt %, about 40 to about 60 wt %, or about 45 wt % to about 55 wt % of the alkyl triglyceride composition, based on the combined weights of the alkyl triglyceride composition and the combination of cyclohexanedicarboxylic acid ester and/or cyclohexanepolycarboxylic acid esters and at least one fast fusing plasticizer. Other specific compositions include compositions having combinations of the upper and lower limits enumerated above.

Other plasticizers that can be used as secondary plasticizers in combination with the alkyl triglycerides prepared from $C_5$ to $C_{10}$ acids with low levels of branching include di-2-ethylhexyl phthalate (DEHP), di-2-ethylhexyl adipate (DEHA), diisononyl phthalate (DINP), diisodecyl phthalate (DIDP), di-2-propylheptyl phthalate (DPHP), diisononylcyclohexanediacid ester (DINCH), butyl benzyl phthalate, di-2-ethylhexyl terephthalate (DOTP), dibutyl terephthalate (DBT), dipropylene glycol dibenzoate, isodecyl benzoate, diisohepty terephthalate, and one or more alkyl benzoates, particularly benzoates where the alkyl group has 8-11, preferably 10, carbon atoms, and the like. In some such plasticizer compositions, the alkyl triglyceride composition comprises from about 1 wt % to about 99 wt % and about 99 wt % to about 1 wt % of one or more of di-2-ethylhexyl phthalate (DEHP), di-2-ethylhexyl adipate (DEHA), diisononyl phthalate (DINP), diisodecyl phthalate (DIDP), di-2-propylheptyl phthalate (DPHP), diisononylcyclohexanediacid ester (DINCH), butyl benzyl phthalate, di-2-ethylhexyl terephthalate (DOTP), dibutyl terephthalate (DBT), dipropylene glycol dibenzoate, isodecyl benzoate, diisohepty terephthalate in the plasticizer composition, based on the combined weights of the alkyl triglyceride composition and any di-2-ethylhexyl phthalate (DEHP), di-2-ethylhexyl adipate (DEHA), diisononyl phthalate (DINP), diisodecyl phthalate (DIDP), di-2-propylheptyl phthalate (DPHP), diisononylcyclohexanediacid ester (DINCH), butyl benzyl phthalate, di-2-ethylhexyl phthalate (DOTP), dibutyl terephthalate (DBT), dipropylene glycol dibenzoate, isodecyl benzoate, and diisohepty terephthalate. In other embodiments, the lower limit of the alkyl triglyceride composition in the plasticizer compositions is at least about 10 wt %, at least about 20 wt %, at least about 30 wt %, at least about 40 wt %, at least about 50 wt %, at least about 60 wt %, at least about 65 wt %, at least about 70 wt %, at least about 75 wt %, at least about 80 wt %, at least about 85 wt %, at least about 90 wt %, or at least about 95 wt % of the plasticizer composition. The upper limit of the alkyl triglyceride composition in the plasticizer compositions can be less than about 10 wt %, less than about 20 wt %, less than about 30 wt %, less than about 40 wt %, less than about 50 wt %, less than about 60 wt %, less than about 65 wt %, less than about 70 wt %, less than about 75 wt %, less than about 80 wt %, less than about 85 wt %, less than about 90 wt %, or less than about 95 wt % of the plasticizer composition. In some embodiments the plasticizer composition comprises from about 10 wt % to about 90 wt %, about 20 wt % to about 80 wt %, 30 wt % to about 70 wt %, about 40 to about 60 wt %, or about 45 wt % to about 55 wt % of the alkyl triglyceride composition. Other specific compositions include compositions having combinations of the upper and lower limits enumerated above.

In other embodiments of this invention, the alkyl triglycerides described herein can be prepared with blends of acids. In the course of this investigation, it was found that the preferred range for carbon number average of the acids containing low levels of branching was about 6 to 8, preferably 6.3 to 7.8, more preferably 6.6 to 7.7. This can be obtained for example, through the esterification of glycerol with a $C_7$ acid having low branching, or through use of a 50/50 mixture of $C_6$ and $C_8$ acids or through a 50/50 mixture of $C_5$ and $C_9$ acids or through a combination of any of the $C_5$ to $C_{10}$ acids, where the weight fractions of the acids is chosen to give an average carbon number between 6 and 8, preferably 6.3 to 7.8, and even more preferably 6.6 to 7.7.

In other embodiments of this invention, the plasticizing esters of this invention can be prepared though blends of acids based on branching and carbon number. For example a plasticizer prepared from the esterification of glycerol using a 50/50 mixture of n-pentanoic acid and 2-propylheptanoic acid, would give a plasticizing ester with an average carbon number side chain of 7.5 and having an average branching number of 0.5. In another example of this invention, an ester prepared by the esterification of glycerol with a 60/40 mixture of n-hexanoic acid and a $C_9$ acid having a branching level of 1.5 would give a plasticizing ester with an average carbon number of 7.2 and having an average branching number of 0.64. These examples are meant to be illustrative of the ability to use acids of varying carbon numbers and varying branching and are not meant to be restrictive to only these particular examples.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

What is claimed is:

1. A composition comprising:
   (i) a triglyceride according to the formula

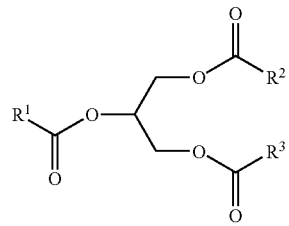

wherein each of $R^1$, $R^2$, and $R^3$ are independently selected from linear $C_4$ to $C_{10}$ alkyl groups and wherein the average branching on said alkyl groups is from about 0.05 to less than 0.8 branches per alkyl group in the triglyceride;
   (ii) at least one ester selected from the group consisting of $C_4$, $C_5$, $C_6$, and $C_7$ secondary aliphatic alcohol esters of cyclohexanecarboxylic acid; and
   (iii) a resin selected from vinyl chloride resins, polyesters, polyurethanes, ethylene-vinyl acetate copolymer, rubbers, acrylics, and mixtures thereof.

2. The composition according to claim 1 further including di-2-propylheptyl phthalate or di-isonongl cyclohexanedicarboxylic acid.

3. The composition according to claim 1 further including a conventional plasticizer selected from the group consisting of phthalates, benzoates, polyester polymeric plasticizers, cyclohexanediacid esters, and terephthalates.

4. The composition of claim 3 wherein the composition is a plastisol.

* * * * *